United States Patent
Kanasaki et al.

(10) Patent No.: US 9,931,715 B2
(45) Date of Patent: Apr. 3, 2018

(54) METHOD FOR DETERMINING CHARACTERISTIC STRESS OF WELDING STRUCTURE, METHOD FOR DESIGNING WELDED STRUCTURE, AND METHOD FOR MANUFACTURING WELDED STRUCTURE

(71) Applicant: MITSUBISHI HEAVY INDUSTRIES, LTD., Tokyo (JP)

(72) Inventors: Hiroshi Kanasaki, Tokyo (JP); Naoki Ogawa, Tokyo (JP); Takaharu Maeguchi, Tokyo (JP); Takao Tsuruta, Tokyo (JP); Takafumi Hiro, Tokyo (JP); Tomoyuki Inoue, Tokyo (JP); Kosuke Kitamura, Tokyo (JP); Tomohisa Ota, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 33 days.

(21) Appl. No.: 15/029,905

(22) PCT Filed: Nov. 28, 2014

(86) PCT No.: PCT/JP2014/081603
§ 371 (c)(1),
(2) Date: Apr. 15, 2016

(87) PCT Pub. No.: WO2015/080261
PCT Pub. Date: Jun. 4, 2015

(65) Prior Publication Data
US 2016/0279739 A1    Sep. 29, 2016

(30) Foreign Application Priority Data
Nov. 29, 2013    (JP) .................... 2013-247968

(51) Int. Cl.
B23K 31/02    (2006.01)
G01L 1/00    (2006.01)
(Continued)

(52) U.S. Cl.
CPC ............ B23K 31/12 (2013.01); B23K 9/0256 (2013.01); B23K 9/232 (2013.01); B23K 31/02 (2013.01);
(Continued)

(58) Field of Classification Search
CPC ...... B23K 31/12; B23K 31/02; B23K 9/0256; B23K 9/232; B23K 31/125;
(Continued)

(56) References Cited

U.S. PATENT DOCUMENTS 2,187,525 A * 1/1940 Houdremont ........... C22C 38/46
219/137 R
2002/0043111 A1 * 4/2002 Takagi .................... C22C 38/04
73/760

(Continued)

FOREIGN PATENT DOCUMENTS

JP    50-090548 A    7/1975
JP    59-169697 A    9/1984
(Continued)

OTHER PUBLICATIONS

International Search Report dated Mar. 3, 2015, issued in couterpart International Application No. PCT/JP2014/081603, with English translation. (4 pages).

(Continued)

Primary Examiner — Kiley Stoner
(74) Attorney, Agent, or Firm — Westerman, Hattori, Daniels & Adrian, LLP

(57) ABSTRACT

A test piece preparation step of preparing a test piece (50) including a welding structure in which a welding material
(Continued)

formed of an austenitic alloy is welded to a member formed of low-alloy steel or low-carbon steel, a hydrogen supply step of supplying hydrogen to the test piece (50), and a characteristic stress acquisition step of applying a load (F) to the test piece (50) to which hydrogen was supplied and acquiring a characteristic stress showing material mechanical properties of the test piece (50) are executed.

22 Claims, 10 Drawing Sheets

(51) Int. Cl.

| | | |
|---|---|---|
| *G01N 3/00* | (2006.01) | |
| *B23K 31/12* | (2006.01) | |
| *B23K 9/025* | (2006.01) | |
| *B23K 9/23* | (2006.01) | |
| *G01N 3/08* | (2006.01) | |
| *G01L 1/22* | (2006.01) | |
| *G01L 5/00* | (2006.01) | |
| *C23C 8/08* | (2006.01) | |
| *B23K 101/12* | (2006.01) | |
| *B23K 101/34* | (2006.01) | |
| *B23K 103/04* | (2006.01) | |
| *B23K 103/18* | (2006.01) | |

(52) U.S. Cl.
CPC .............. *B23K 31/125* (2013.01); *C23C 8/08* (2013.01); *G01L 1/2218* (2013.01); *G01L 5/0033* (2013.01); *G01N 3/08* (2013.01); *B23K 2201/12* (2013.01); *B23K 2201/34* (2013.01); *B23K 2203/04* (2013.01); *B23K 2203/05* (2015.10); *B23K 2203/18* (2013.01); *G01N 2203/0067* (2013.01); *G01N 2203/0236* (2013.01); *G01N 2203/0296* (2013.01); *G01N 2203/0298* (2013.01)

(58) Field of Classification Search
CPC ............ B23K 2203/05; B23K 2203/18; B23K 2203/04; B23K 2201/34; B23K 2201/12; B23K 2203/02; C23C 8/08; G01L 5/0033; G01L 1/2218; G01N 3/08; G01N 2203/0236; G01N 2203/0296; G01N 2203/0067

USPC .............. 228/102–105, 8–12, 262.4–262.41; 73/760–780
See application file for complete search history.

(56) References Cited

U.S. PATENT DOCUMENTS

| | | | | |
|---|---|---|---|---|
| 2005/0016980 | A1* | 1/2005 | Hara | B23K 9/0253 219/137 WM |
| 2006/0191606 | A1* | 8/2006 | Ogawa | B23K 9/173 148/327 |
| 2008/0226491 | A1* | 9/2008 | Satou | B23K 11/0873 420/90 |
| 2008/0308198 | A1* | 12/2008 | Sakaguchi | C21D 6/001 148/608 |
| 2011/0100131 | A1* | 5/2011 | Brown | G01M 5/0033 73/761 |
| 2011/0136239 | A1* | 6/2011 | Hehn | G01N 3/20 436/6 |
| 2013/0316191 | A1* | 11/2013 | Kawasaki | B23K 9/0026 428/679 |
| 2014/0086786 | A1* | 3/2014 | Nako | B23K 9/02 420/92 |
| 2014/0238145 | A1* | 8/2014 | Tran | G01N 3/20 73/851 |
| 2014/0377123 | A1* | 12/2014 | Nako | B23K 9/173 420/91 |
| 2016/0354870 | A1* | 12/2016 | Jotoku | B23K 9/23 |
| 2016/0363525 | A1* | 12/2016 | Friedersdorf | G01N 3/02 |

FOREIGN PATENT DOCUMENTS

| | | |
|---|---|---|
| JP | 2006-29977 A | 2/2006 |
| JP | 2008-212945 A | 9/2008 |
| JP | 2009-69004 A | 4/2009 |
| JP | 2012-115886 A | 6/2012 |
| JP | 2012-196686 A | 10/2012 |

OTHER PUBLICATIONS

Translation of Written Opinion dated Mar. 3, 2015, issued in couterpart International Application No. PCT/JP2014/081603, with English translation. (15 pages).

* cited by examiner

METHOD FOR DETERMINING CHARACTERISTIC STRESS OF WELDING STRUCTURE, METHOD FOR DESIGNING WELDED STRUCTURE, AND METHOD FOR MANUFACTURING WELDED STRUCTURE

TECHNICAL FIELD

The present invention relates to a method for determining the characteristic stress of a welding structure, a method of designing a welded structure including the welding structure, and a method of manufacturing a welded structure including the welded structure. Priority is claimed on Japanese Patent Application No. 2013-247968, filed Nov. 29, 2013, the content of which is incorporated herein by reference.

BACKGROUND ART

For example, a welded structure is disclosed in the following Patent Literature 1. This welded structure is a steam generator in a nuclear power plant. This steam generator has a channel head and a partition plate for partitioning an inside of the channel head. The channel head includes a base material formed of low-alloy steel and a cladding (welding material) formed by performing built-up welding of austenitic stainless on a surface of the base material. The partition plate is formed of a nickel-based alloy. This partition plate is welded to the surface of the channel head, that is, the surface of the cladding formed of the austenitic stainless.

CITATION LIST

Patent Literature

Patent Literature 1

Japanese Unexamined Patent Application, First Publication No. 2012-196686

SUMMARY OF INVENTION

Technical Problem

When a welded structure including a welding structure is designed, it is preferable to recognize material mechanical properties in the vicinity of a boundary between a base material and a welding member such as a cladding, for example, a characteristic stress such as fracture stress or tensile strength as accurately as possible.

Therefore, an object of the present invention is to provide a method of determining a characteristic stress of a welding structure, particularly, a welding structure in which a welding member including a welding material of an austenitic alloy is welded to a member formed of low-alloy steel or low-carbon steel, a method of designing a welded structure including the welding structure, and a method of manufacturing a welded structure including the welded structure.

Solution to Problem

As an aspect according to the invention for accomplishing the above-described objective, a method of determining a characteristic stress of a welding structure includes a test piece preparation step of preparing a test piece including a welding structure in which a welding material formed of an austenitic alloy is welded to a member formed of low-alloy steel or low-carbon steel; a hydrogen supply step of supplying hydrogen to the test piece; and a characteristic stress acquisition step of applying a load to the test piece to which hydrogen was supplied and acquiring the characteristic stress showing material mechanical properties of the test piece.

The inventors discovered the following facts about the welding structure in which a welding material formed of an austenitic alloy is welded to a member formed of the low-alloy steel or the low-carbon steel.

(1) When the austenitic alloy is used as the welding material, hydrogen formed from the moisture in the air may be retained within a system in a welding step.

(2) The hydrogen retained in the austenitic alloy is diffused when an ambient temperature increases.

(3) When a member which is a welding target of the welding material is formed of low-alloy steel or low-carbon steel, the hydrogen retained in the austenitic alloy which is the welding material moves to the member side.

(4) When the hydrogen moves to the member side, hydrogen embrittlement occurs in the vicinity of a boundary of low-alloy steel or low-carbon steel. As a result, the strength in the vicinity of the boundary with the welding material in the member decreases.

According to the above information, the inventors determined a characteristic stress showing material mechanical properties in the welding structure of the above welded structure in the above-described determination method before the welded structure is designed.

In the method of determining the characteristic stress, it is possible to obtain the characteristic stress of the above-described welding structure. Consequently, it is possible to suppress damage to the welding structure by hydrogen embrittlement by designing and manufacturing a welded structure on the basis of the characteristic stress.

In the method of determining the characteristic stress of the welding structure, the hydrogen supply step may be executed while the characteristic stress acquisition step is executed. Also, the hydrogen supply step may be executed before the characteristic stress acquisition step is executed. Also, the hydrogen supply step may be continuously executed while the characteristic stress acquisition step is executed, from a time before the execution of the characteristic stress acquisition step.

In the method of determining the characteristic stress of the welding structure according to any one described above, in the hydrogen supply step, the hydrogen may be supplied to the test piece by arranging the test piece in an aqueous solution including hydrogen ions and setting the test piece as a negative electrode.

In the method of determining the characteristic stress, it is possible to easily adjust an amount of hydrogen supply to the test piece while supplying hydrogen to the test piece in a simple facility.

In the method of determining the characteristic stress of the welding structure according to any one described above for supplying the hydrogen to the test piece from a time before the character stress acquisition step, in the hydrogen supply step, the hydrogen may be supplied to the test piece by arranging the test piece in an aqueous solution including hydrogen ions and setting the test piece as a negative electrode, and, according to the execution of the hydrogen supply step, a hydrogen supply condition including an execution time of the hydrogen supply step to be executed before the characteristic stress acquisition step may be determined so that a hydrogen concentration of a part formed of the low-alloy steel or the low-carbon steel in the test piece is greater than or equal to a hydrogen concentration assumed to be a maximum hydrogen concentration in a part of a boundary side with a welding member in a member in an actual welded structure including the welding structure.

In the method of determining the characteristic stress, it is possible to easily adjust an amount of hydrogen supply to the test piece while supplying hydrogen to the test piece in a simple facility. Further, it is possible to obtain the characteristic stress under a more strict condition than in a hydrogen embrittlement environment in an actual welded structure in the method of determining the characteristic stress.

Also, in the method of determining the characteristic stress of the welding structure according to any one described above, after a test piece base material including the welding structure in which the welding material is welded to the member formed of low-alloy steel or low-carbon steel is prepared in the test piece preparation step, a part including a boundary between the low-alloy steel or the low-carbon steel and the welding material may be acquired as the test piece from the test piece base material.

In the method of determining the characteristic stress, it is possible to easily set a shape of the test piece as a desired shape by obtaining the test piece from a test piece member.

In the method of determining the characteristic stress of the welding structure according to any one described above, the characteristic stress acquired in the characteristic stress acquisition step may be fracture stress.

As an aspect according to the invention for accomplishing the above-described object, a method of designing a welded structure includes the method of determining the characteristic stress of the welding structure according to any one described above; and a design step of designing the welded structure so that maximum stress occurring in the welding structure is less than the characteristic stress determined in the method of determining the characteristic stress of the welding structure in welded structures including the welding structure.

Here, in the method of designing the welded structure serving as the first aspect, the welded structure may include a first member formed of the low-alloy steel or the low-carbon steel, a welding member formed of the welding material built-up welded to a surface of the first member, and a second member welded to a surface of the welding member, and a thickness dimension of the welding member built-up welded to the surface of the first member may be determined such that a maximum stress occurring in the welding structure of the welded structure is less than the characteristic stress in the design step.

Also, in the method of designing the welded structure serving as the first aspect, the welded structure may include a first member formed of the low-alloy steel or the low-carbon steel, a first welding member formed of a first welding material serving as the welding material built-up welded to the surface of the first member, and a second member welded to the surface of the first welding member via a second welding material, the first member may have a concave portion formed in a member formed of the low-alloy steel or the low-carbon steel by cutting a surface of the member, a side surface of the concave portion may be inclined gradually toward an outer side of the concave portion as the side surface of the concave portion approaches an uncut surface, the surface of the first member for built-up welding the first welding material may be a bottom surface and a side surface of the concave portion, and, in the design step, a region in which there is a side surface of the concave portion in a first direction in which a surface around the concave portion may be widened is separated from a position in the first direction in which a surface of a second welding member formed of the second welding material is in contact with a surface of the first welding member.

Also, in the method of designing the welded structure serving as the first aspect, the welded structure may include a first member formed of the low-alloy steel or the low-carbon steel, a first welding member formed of a first welding material serving as the welding material built-up welded to the surface of the first member, and a second member welded to the surface of the first welding member via a second welding material, the first member may have a concave portion formed in the member by cutting a surface of a member formed of the low-alloy steel or the low-carbon steel, a side surface of the concave portion may be inclined gradually toward an outer side of the concave portion as a side surface of the concave portion approaches an uncut surface, and a bottom surface of the concave portion may be widened in the first direction in which a surface around the concave portion is widened, the surface of the first member for built-up welding the first welding material may be the bottom surface and the side surface of the concave portion, and an angle formed by the side surface inclined to the bottom surface of the concave portion may be determined so that a maximum stress occurring in the welding structure of the welded structure is less than the characteristic stress in the design step.

In the method of designing the welded structure according to any one described above, the welded structure may be a pressure vessel. Further, the pressure vessel may be a vessel in which coolant in a nuclear power plant is accumulated.

As an aspect of the invention for accomplishing the above-described object, a method of manufacturing a welded structure includes the method of designing the welded structure according to any one described above; and a manufacturing step of manufacturing the welded structure according to a result of executing the design method.

Advantageous Effects of Invention

According to an aspect of the present invention, it is possible to obtain a characteristic stress of a welding structure in which a welding material formed of an austenitic alloy is welded to a member formed of low-alloy steel or low-carbon steel. Consequently, it is possible to suppress damage to the welding structure by hydrogen embrittlement by designing and manufacturing a welded structure on the basis of the characteristic stress.

DESCRIPTION OF EMBODIMENTS

Hereinafter, embodiments of the present invention and modified examples thereof will be described with reference to the drawings.

[Welded Structure]

First, an embodiment of a welded structure which is an application target of the present invention will be described.

Figure 13:
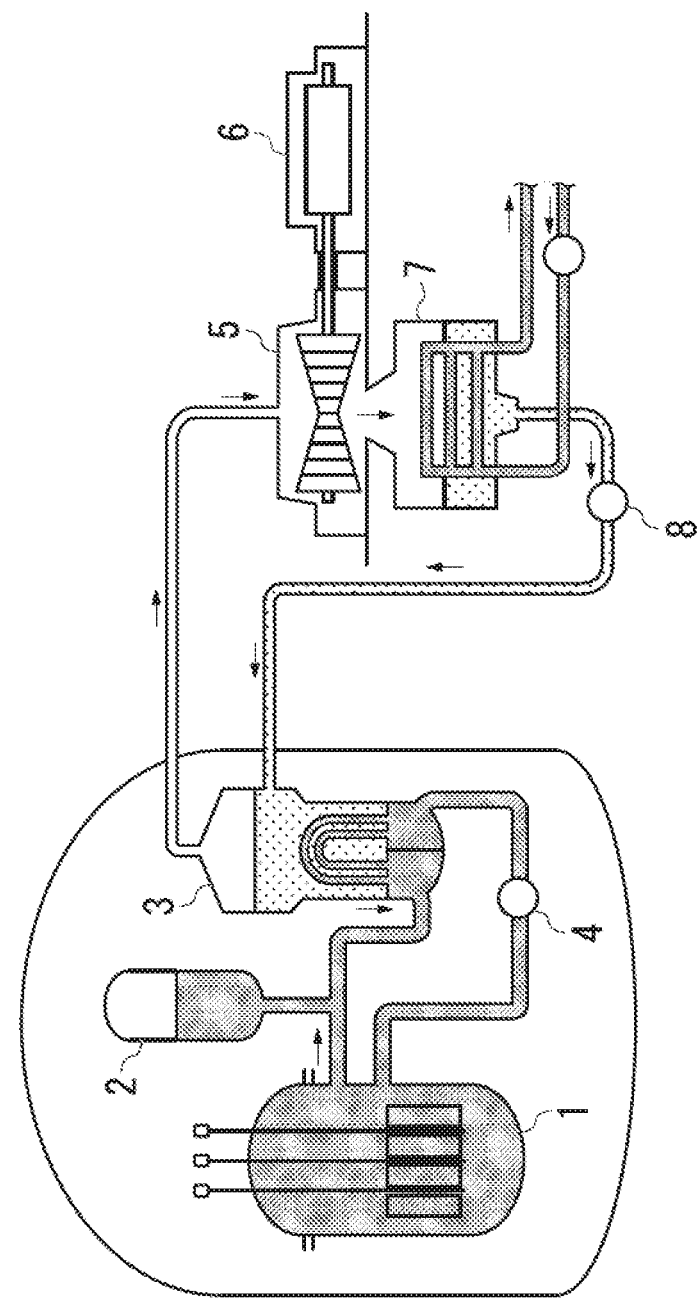
FIG. 13 is a system diagram of a nuclear power plant in an embodiment according to the present invention.

The welded structure of this embodiment is a steam generator of a nuclear power plant. For example, as illustrated in FIG. 13, the nuclear power plant includes a pressurized water nuclear reactor (hereinafter, simply referred to as a nuclear reactor) 1, a pressurizer 2 configured to increase a pressure within the nuclear reactor 1, a steam generator 3 configured to generate steam from water which is a secondary coolant by exchanging heat between a primary coolant and the secondary coolant from the nuclear reactor 1, a coolant pump 4 configured to return the primary coolant passing through the steam generator 3 to the nuclear reactor 1, a steam turbine 5 configured to be driven by the steam generated by the steam generator 3, a power generator 6 configured to generate power using the driving of the steam turbine 5, a condenser 7 configured to convert the steam passing through the steam turbine 5 into water, and a feedwater pump 8 configured to return the water within the condenser 7 to the steam generator 3.

Figure 12:
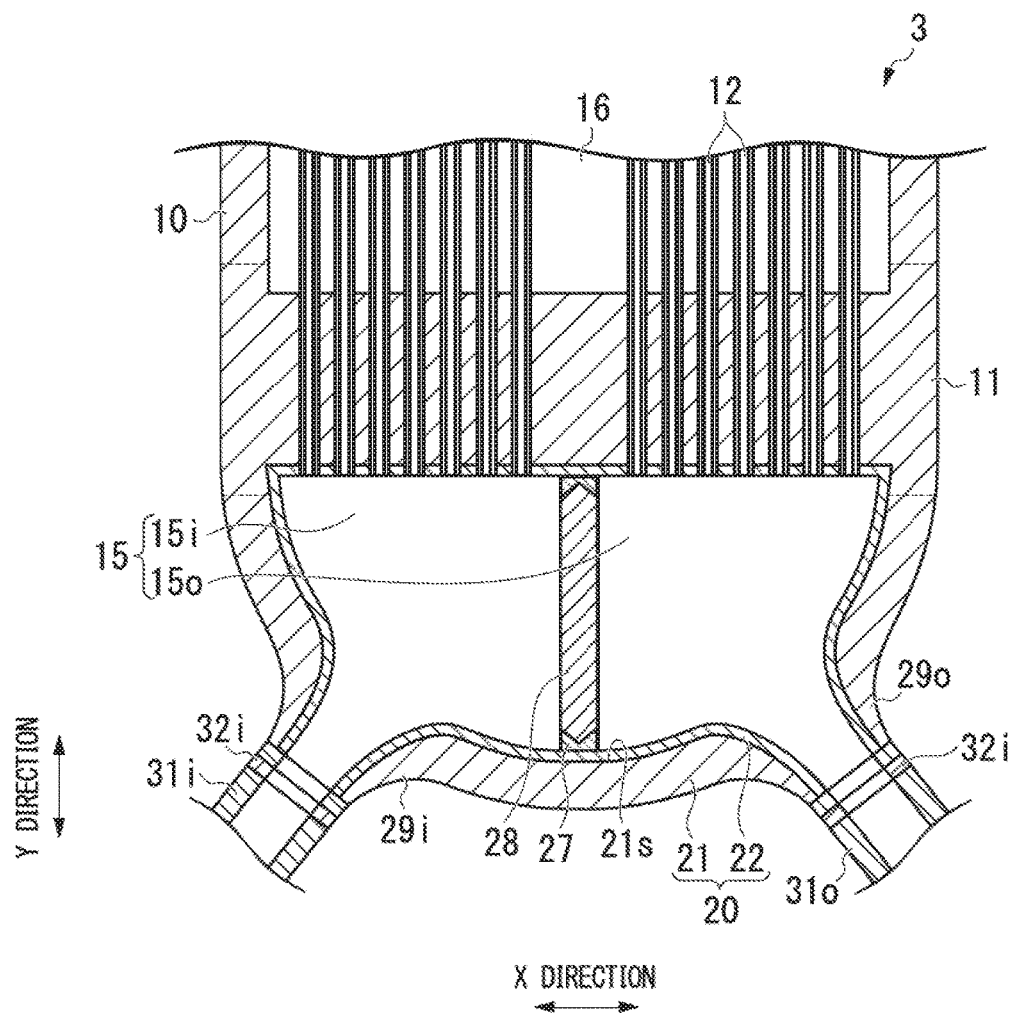
FIG. 12 is a cross-sectional view of main parts of a steam generator serving as a welded structure in an embodiment according to the present invention.

As illustrated in FIG. 12, the steam generator 3 includes a shell 10, a channel head 20 configured to close an end opening of the body 10, a tube plate 11 configured to partition an internal space formed by the body 10 and the channel head 20 into a primary chamber 15 and a secondary chamber 16, a U tube 12 having an end fixed to the tube plate 11 and bent within the secondary chamber 16, and a partition plate 28 configured to partition the primary chamber 15 into an inlet chamber 15i and an outlet chamber 15o.

An inlet nozzle 29i for guiding the primary coolant into the inlet chamber 15i is formed on the inlet chamber 15i side of the channel head 20. A short tubular inlet safe end 31i is joined to the inlet nozzle 29i. Also, an outlet nozzle 29o for causing the primary coolant from the outlet chamber 15o to externally flow is formed on the outlet chamber 15o side of the channel head 20. A short tubular outlet safe end 31o is joined to the outlet nozzle 29o.

The primary coolant heated within the nuclear reactor 1 flows through the inlet chamber 15i within the primary chamber 15 of the steam generator 3 via the inlet safe end 31i. The primary coolant externally flows via the U tube 12, the outlet chamber 15o within the primary chamber 15, and the outlet safe end 31o. Water which is the secondary coolant flows inside the secondary chamber 16. This water is heated by heat exchange with the primary coolant passing through the inside of the U tube 12 arranged within the secondary chamber 16 and the heated water is converted into steam.

The channel head 20 includes a base material (first member) 21 configured to form a channel head main body and a cladding (first welding member) 22 in which a first welding material is built-up welded to the surface of the primary chamber 15 side of the base material 21. The partition plate (second member) 28 is welded to the cladding 22 via a second welding member 27 formed of a second welding material.

Here, for convenience of the following description, a direction in which a surface 21s in the vicinity of the partition plate 28 welded via the cladding 22 as the surface of the primary chamber 15 side of the base material 21 is widened is set as an X direction (first direction) and a direction vertical to the surface 21s is set as a Y direction. The partition plate 28 extends long in the Y direction.

In this embodiment, the base material 21 of the channel head 20 is formed of low-alloy steel having a carbon content ratio of 0.1 mass % or less. Also, the low-alloy steel includes main elements of Cr, Cu, Mo, Ni, etc. in addition to Fe and is alloy steel in which a total amount of the following elements is 5 mass % or less: Al, B, Co, Cr, Cu, La, Mo, Nb, Ni, Pb, Se, Te, Ti, V, W, and Zr The first welding material which forms the cladding 22 is steel use stainless (SUS) 308 which is austenitic stainless. The partition plate 28 is formed of a 690-type nickel-based alloy (for example, INCONEL 690 (INCONEL is a registered trademark of Special Metals Corporation (International Nickel Company))). Also, the second welding material is the same 690-type nickel-based alloy as the material which forms the partition plate 28. Both the inlet safe end 31i and the outlet safe end 31o are formed of SUS 308 which is austenitic stainless. These are all welded to the nozzles 29i and 29o via the welding materials 32i and 32o including SUS 308 which is the same as the material to form the safe ends 31i and 31o.

[Method of Manufacturing Welded Structure]

Figure 1:
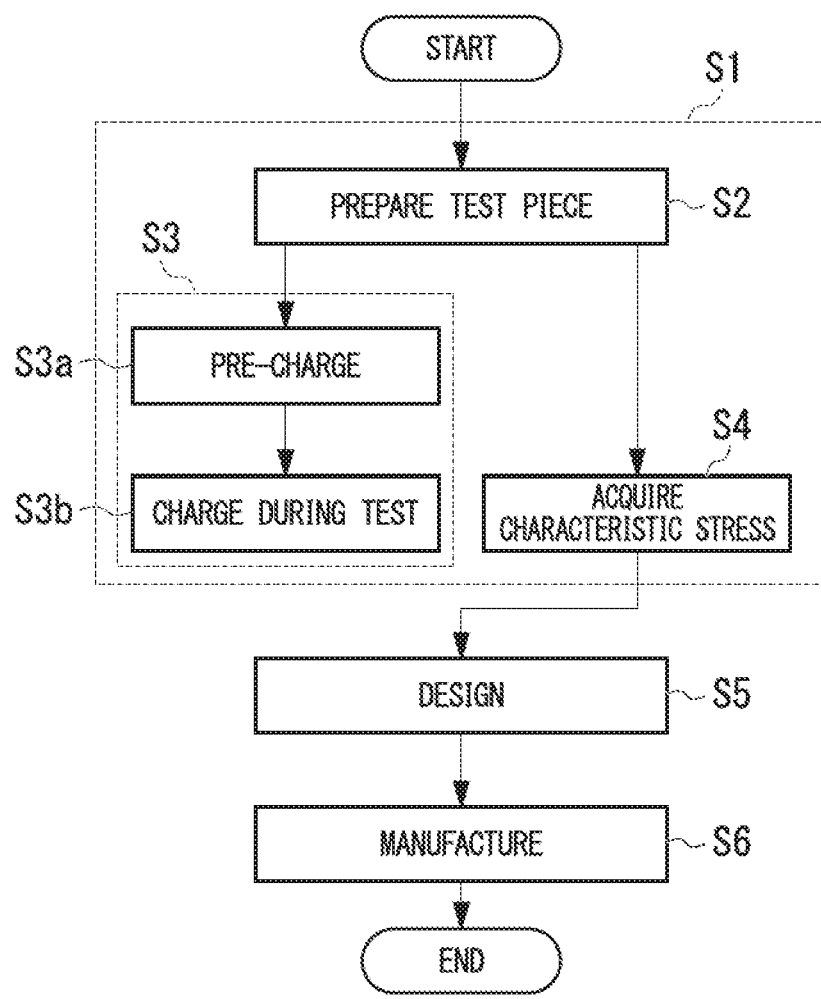
FIG. 1 is a flowchart illustrating a procedure of a method of manufacturing a welded structure in an embodiment according to the present invention.

Next, a method of manufacturing the steam generator 3 serving as the above-described welded structure will be described according to the flowchart illustrated in FIG. 1.

When the steam generator 3 is manufactured, the characteristic stress showing material mechanical properties of a welding structure in the steam generator 3 is first determined (S1: characteristic stress determination step). Here, the welding structure includes the base material 21 of the channel head 20 formed of low-alloy steel and the cladding 22 formed of SUS 308 which is an austenitic stainless type, built-up welded to the primary chamber 15 side of the base material 21.

The inventors discovered the following facts about the welding structure.

(1) When an austenitic alloy is used as a welding material, hydrogen formed from the moisture in the air may be retained within a system in a welding step.

(2) The hydrogen retained in the austenitic alloy is diffused when an ambient temperature increases.

(3) When the base material is formed of low-alloy steel or low-carbon steel, the hydrogen retained in the austenitic alloy which is a welding material moves to the base material side.

(4) When the hydrogen moves to the base material side, hydrogen embrittlement occurs in the vicinity of a boundary of low-alloy steel or low-carbon steel. As a result, the strength in the vicinity of the boundary with the welding material in the base material decreases.

According to the above information, the inventors determined the fracture stress which is one of the characteristic stresses showing material mechanical properties in the above welding structure in the steam generator 3 before the design of the steam generator 3.

Figure 2:
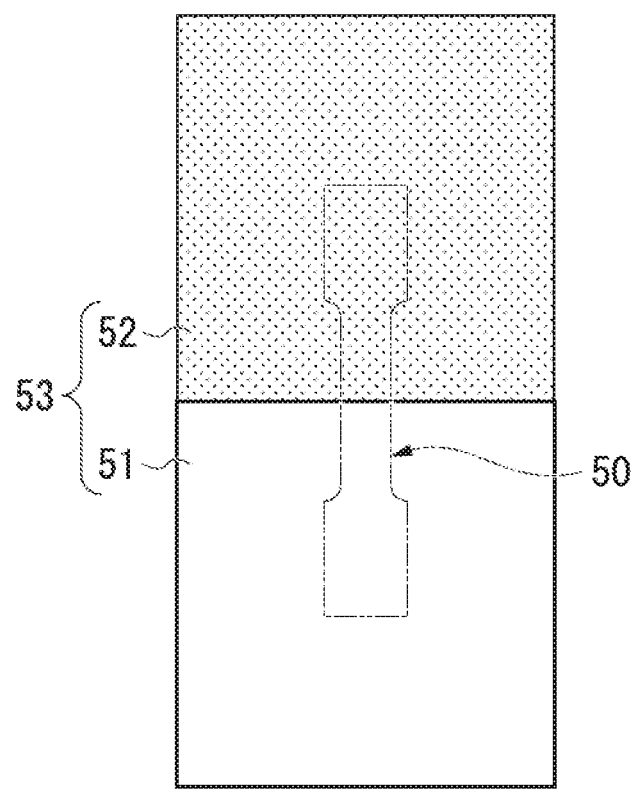
FIG. 2 is an explanatory diagram illustrating a method of preparing a test piece in an embodiment according to the present invention.

In the characteristic stress determination step, a test including a welding structure similar to the above-described welding structure is first prepared (S2: test piece preparation step). Specifically, as illustrated in FIG. 2, a member 51 formed of the low-alloy steel which is the same material as the base material 21 of the channel head 20 is first prepared. Next, the welding member 52 obtained by built-up welding SUS 308 which is the same material as the first welding material is formed on the surface of the member 51 and the test piece base material 53 having the member 51 and the welding member 52 is prepared. A part including a boundary between the member 51 and the welding member 52 is cut as a test piece 50 from the test piece base material 53. The shape of the test piece 50 is, for example, a shape defined in Japan Industrial Standard (JIS) Z 2201.

Next, hydrogen is supplied to the test piece 50 (S3: hydrogen supply step). In this hydrogen supply step S3, the test liquid is prepared. This test liquid is, for example, an aqueous solution of the following composition.

1/3M $H_3BO_3$+1/30M KCl+1/100M thiourea

In the above formula, "M" denotes molarity.

Figure 3:
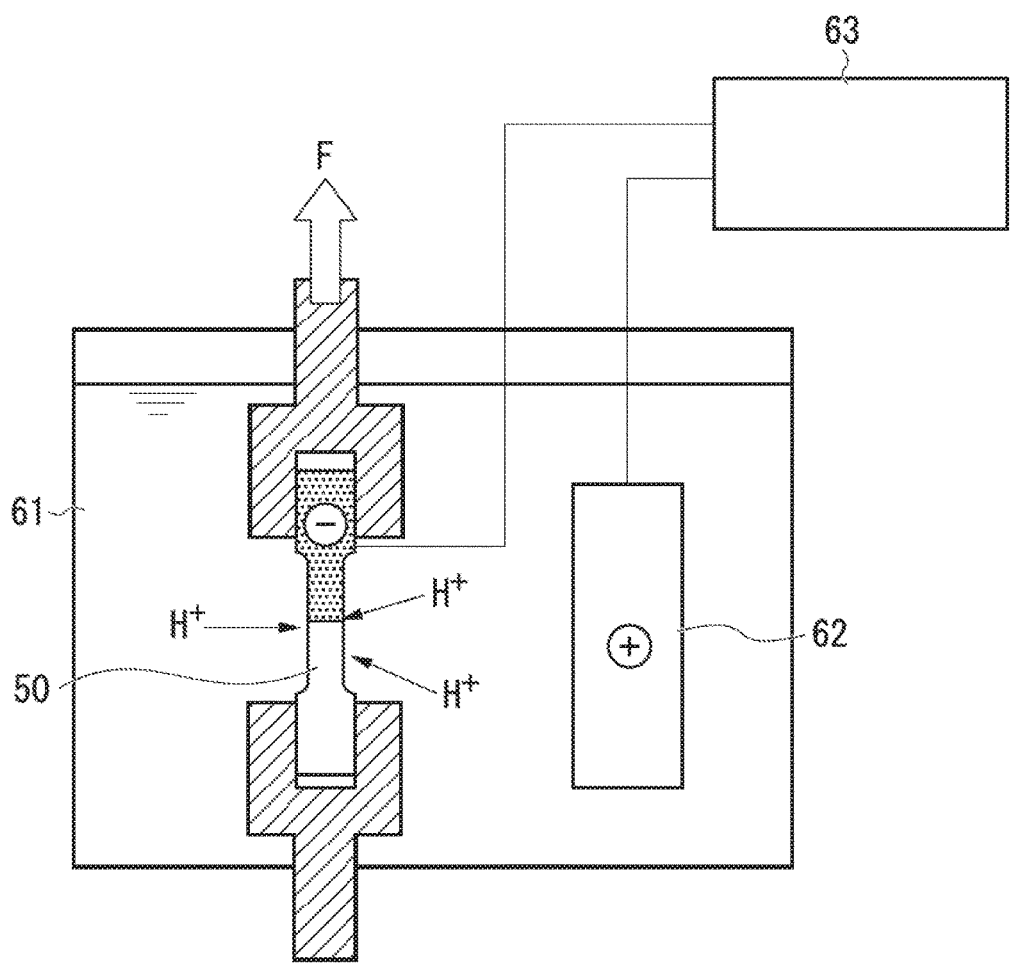
FIG. 3 is an explanatory diagram illustrating a hydrogen supply step and a characteristic stress acquisition step in an embodiment according to the present invention.

As illustrated in FIG. 3, the test piece 50 is immersed in the above test liquid 61, this test piece 50 is set as a working electrode, and a counter electrode 62 formed of Pt is immersed in the test liquid 61. A voltage is applied by a potentiostat 63 between the test piece 50 which is the working electrode and the counter electrode 62. As a result, the working electrode which is the test piece 50 becomes a negative electrode and hydrogen ions in the test liquid 61 are supplied to the test piece 50. At this time, a current density in the test liquid 61 is, for example, 10 mA/cm$^2$.

Figure 4:
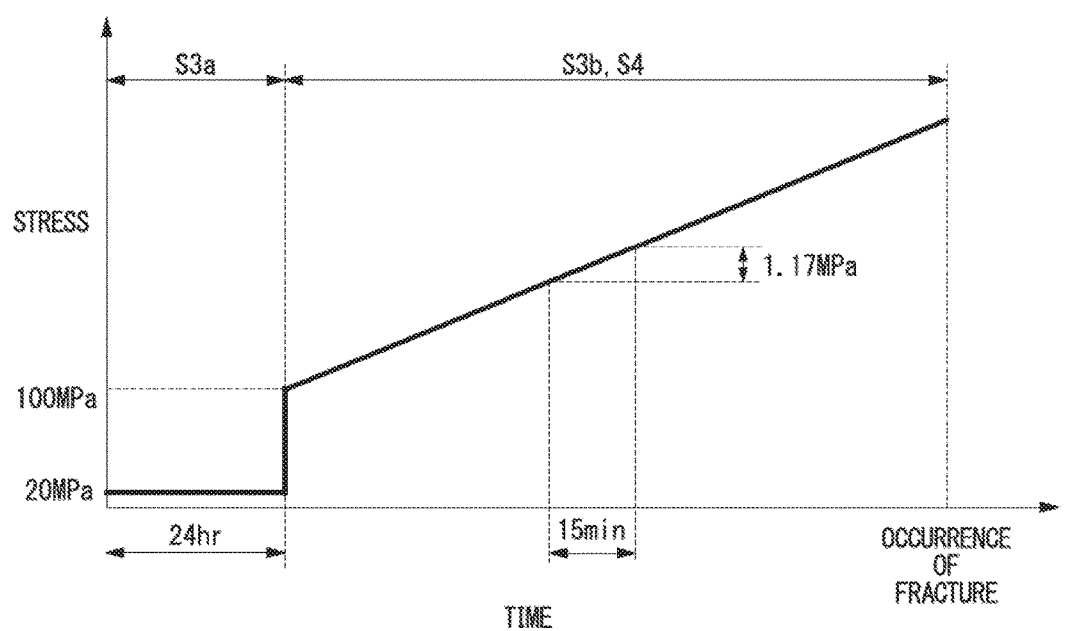
FIG. 4 is a graph illustrating a change in stress occurring in a test piece according to a temporal change during the hydrogen supply step in an embodiment according to the present invention.

Next, as illustrated in FIG. 3, a tensile test is performed by applying a tensile load F to the test piece 50 and fracture stress which is one of the characteristic stresses is acquired (S4: characteristic stress acquisition step). As illustrated in FIG. 4, in this embodiment, a pre-charging step S3$a$ of supplying hydrogen to the test piece 50 is executed before the tensile test is performed and a charging step S3$b$, during the test, for supplying the hydrogen to the test piece 50 are executed. That is, the hydrogen supply step S3 of this embodiment includes the pre-charging step S3$a$ and the charging step S3$b$ during the test. The composition of the test liquid 61 and the current density of the test liquid 61 in the pre-charging step S3$a$ during the test are substantially the same as the composition of the test liquid 61 and the current density of the test liquid 61 in the charging step S3$b$.

In the pre-charging step S3$a$, for example, as tensile load is applied to generate a tensile stress of 20 megapascals (MPa) in the test piece 50 so that the test piece 50 is stably held by a chuck and this state is maintained, for example, for 24 hours. Also, although the tensile load is applied to the test piece so as to stably hold the test piece 50 in the pre-charging step S3$a$, it is unnecessary to apply the tensile load to the test piece 50 when the test piece 50 is stably held even when no tensile load is applied.

At a point in time at which 24 hours have elapsed from the start of the pre-charging step S3$a$, that is, at a point in time at which the pre-charging step S3$a$ ends, the tensile load is applied to the test piece 50, for example, so that a tensile stress of 100 MPa occurs, and the characteristic stress acquisition step S4 and the charging step S3$b$ during the test start. In this characteristic stress acquisition step S4, the tensile load F during the tensile test is gradually increased so that the tensile stress generated in the test piece 50 increases, for example, at a rate of 1.17 MPa per 15 minutes.

When a fracture occurs in the test piece 50 while the tensile load F increases, the stress at a point in time at which the crack occurs becomes the fracture stress of the test piece 50. Also, although the fracture stress is acquired as one of the characteristic stresses here, a characteristic stress such as tensile strength or yield stress may be acquired.

The test liquid 61 in the pre-charging step S3$a$, the current density of the test liquid 61, and a hydrogen supply condition in an execution time or the like of the pre-charging step S3$a$ are determined, for example, as follows. According to the execution of the pre-charging step S3$a$, the hydrogen supply condition is determined so that the hydrogen concentration of the part formed of low-alloy steel in the test piece 50 is greater than or equal to a hydrogen concentration assumed to be a maximum hydrogen concentration in the vicinity of a boundary with the cladding 22 in the base material 21 of the channel head 20 of the steam generator 3.

Consequently, at a point in time at which the pre-charging step S3$a$ of the hydrogen supply step S3 is completed, the hydrogen concentration of the part formed of the low-alloy steel in the test piece 50 is greater than or equal to the hydrogen concentration assumed to be the maximum hydrogen concentration (hereinafter, referred to as an actual maximum hydrogen concentration) in the vicinity of the boundary with the cladding 22 in the base material 21 of the channel head 20 of the steam generator 3. Consequently, in this embodiment, the charging step S3$b$ during the test in the hydrogen supply step S3 is executed to prevent the hydrogen concentration of the part formed of the low-alloy steel in the test piece 50 from decreasing during the characteristic stress acquisition step S4.

However the charging step S3$b$ during the test may be omitted when the hydrogen concentration of the part formed of the low-alloy steel in the test piece 50 is greater than or equal to the actual maximum hydrogen concentration between some time before the fracture occurs in the test piece 50 in the characteristic stress acquisition step S4 and a fracture occurrence time even when the charging step S3$b$ during the test is not executed. Also, the pre-charging step S3$a$ may be omitted when the hydrogen concentration of the part formed of the low-alloy steel in the test piece 50 is greater than or equal to the actual maximum hydrogen concentration in the execution of the charging step S3$b$ during the test between some time before the fracture occurs in the test piece 50 in the characteristic stress acquisition step S4 and the fracture occurrence time even when the pre-charging step S3$a$ is not executed.

However, it is possible to accurately acquire a characteristic stress of the welding structure affected by hydrogen embrittlement when the hydrogen concentration of the part formed of the low-alloy steel in the test piece 50 is greater than or equal to the actual maximum hydrogen concentration at the point in time at which the tensile test starts and this state also continues during the tensile test. Thus, in the hydrogen supply step S3, it is preferable to execute the charging step S3a during the test and the charging step S3b during the test.

When a characteristic stress of the above-described welded structure is acquired in the characteristic stress acquisition step S4, the welded structure including the welding structure, that is, the steam generator 3, is designed (S5: design step). In this design step S5, the steam generator 3 is designed so that the maximum stress occurring in the welding structure of the steam generator 3 is less than the characteristic stress acquired in the characteristic stress acquisition step S4 or, here, less than the fracture stress.

Figure 6:
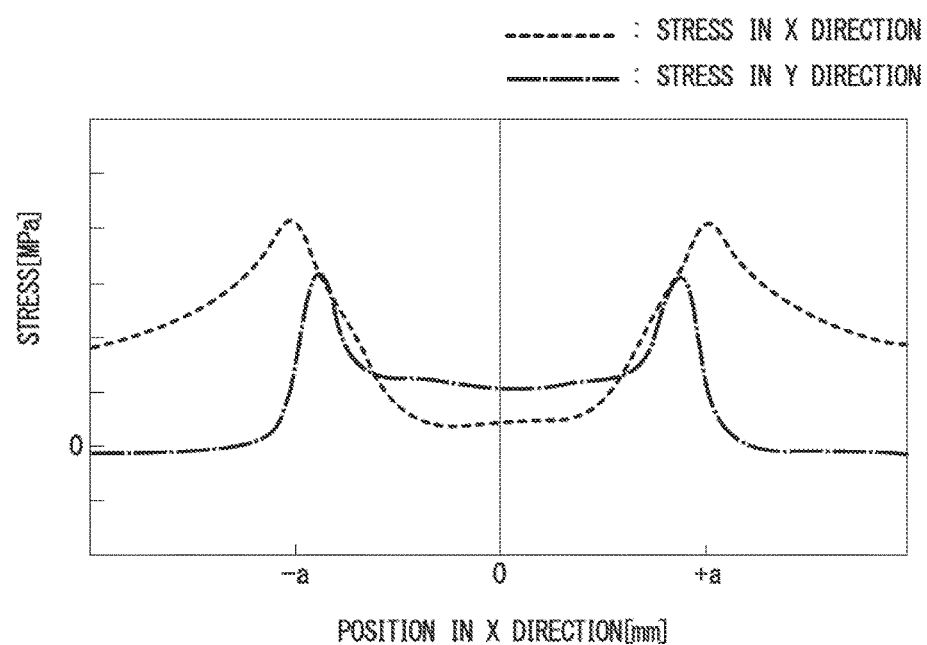
FIG. 6 is a graph illustrating the stress occurring at respective positions in the welding structure illustrated in FIG. 5.

If the steam generator 3 is designed without considering the fracture stress which occurs in the welding structure acquired in the characteristic stress acquisition step S4, the stress illustrated in FIG. 6 is assumed to occur at each position of the boundary between the base material 21 and the cladding 22 in the welding structure of the steam generator 3 as a result of stress analysis. Also, in FIG. 6, the horizontal axis represents a position in an X direction and the vertical axis represents a stress. Also, in FIG. 6, a broken line represents a stress in the X direction and a one-dot chain line represents a stress in the Y direction.

Figure 5:
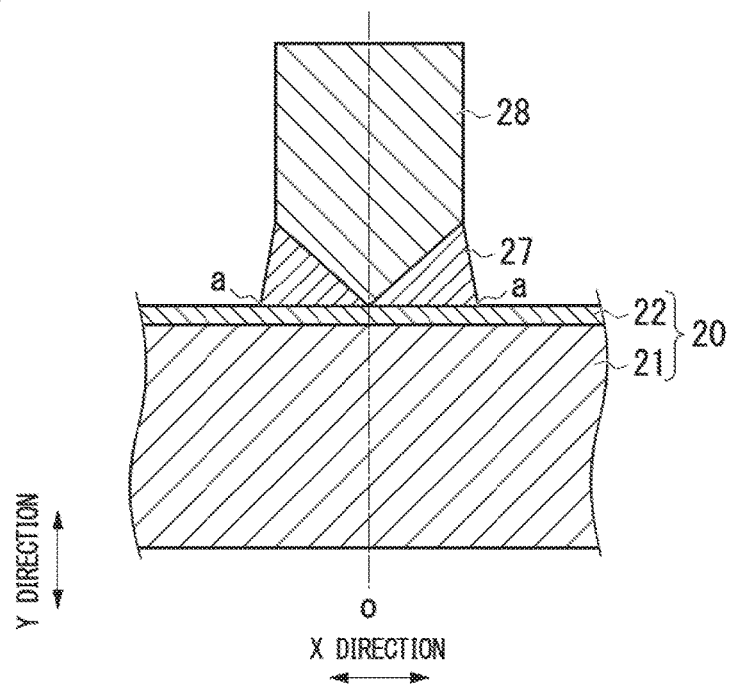
FIG. 5 is a cross-sectional view of a welding structure in an embodiment according to the present invention.

As illustrated in FIG. 6, both maximum values of the stress in the X direction and the stress in the Y direction occur in the vicinity of stress concentration positions. The stress concentration position is a contact position a between the surface of the cladding (first welding member) 22 formed of the first welding material (SUS 308) and the surface of the second welding member 27 formed of the second welding material (690-type nickel-based alloy) as illustrated in FIG. 5.

A breakdown in the boundary between the base material 21 and the cladding 22 in the welding structure may occur when the stress in the direction vertical to the boundary surface, that is, the stress in the Y direction, is greater than or equal to the fracture stress. If the fracture stress obtained in the characteristic stress acquisition step S4 is 380 MPa and the maximum stress in the Y direction obtained in the stress analysis is 400 MPa and is greater than or equal to the fracture stress, the maximum stress in the Y direction is redesigned to be less than the fracture stress.

Figure 7:
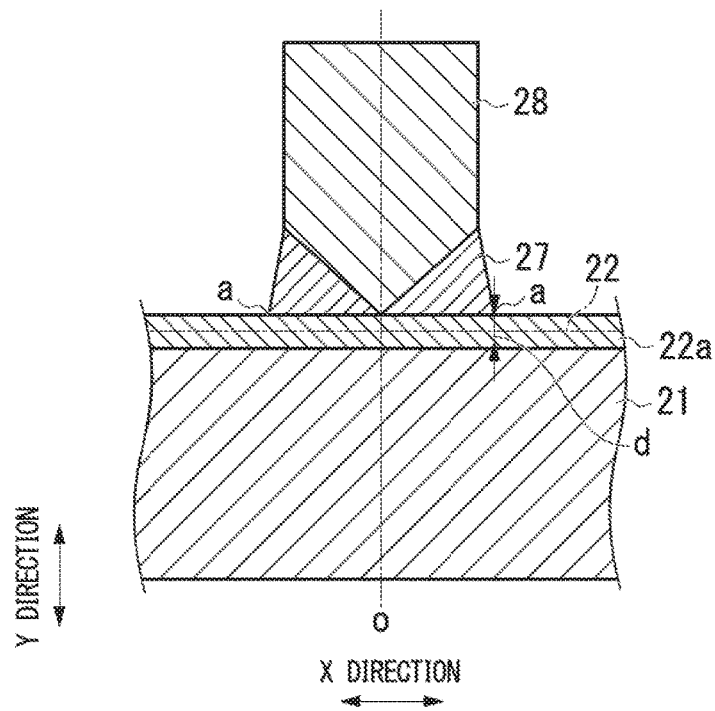
FIG. 7 is a cross-sectional view after a change in a design of the welding structure in an embodiment according to the present invention.

Specifically, as illustrated in FIG. 7, a distance d from the above-described stress concentration position a to the boundary between the base material 21 and a cladding 22a increases by increasing the thickness (a dimension in the Y direction) of the cladding 22a formed of the first welding material.

When the design step S5 ends, the steam generator 3 is manufactured on the basis of a design result determined in the design step S5 (S6: manufacturing step).

As described above, in this embodiment, it is possible to suppress damage to the welding structure by hydrogen embrittlement because a characteristic stress is obtained by applying a load in a state in which hydrogen is supplied to the test piece 50 including the welding structure and the steam generator 3 which is the welded structure is designed and manufactured on the basis of the characteristic stress.

[Modified example]

Figure 8:
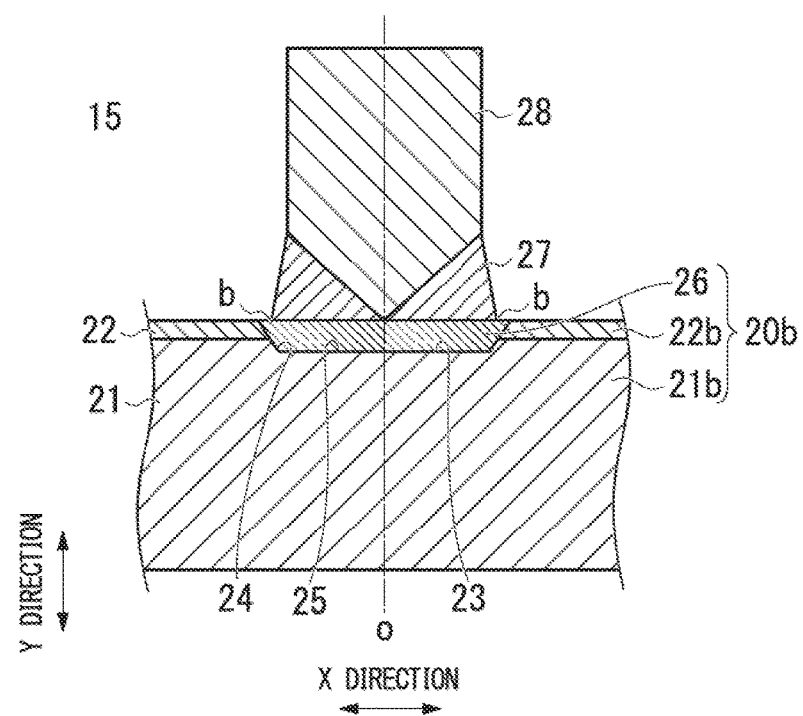
FIG. 8 is a cross-sectional view of a welding structure in a modified example of the embodiment according to the present invention.

In the above embodiment, a partition plate 28 serving as a second member is welded to a cladding 22 formed of SUS 308 via a second welding material. However, as illustrated in FIG. 8, for example, parts of the cladding 22 formed of SUS 308 and a base material 21 are cut and a 690-type nickel-based alloy serving as a third welding material is built-up welded to the cut parts, and the partition plate 28 serving as the second member may be welded to a joint cladding (third welding member) 26 formed of the third welding material via the second welding material.

Specifically, a concave portion 23 concaved outward is formed on the primary chamber 15 side of the channel head 20 of the above-described embodiment by cutting the parts of the cladding 22 formed of SUS 308 and the base material 21. A side surface 24 of the concave portion 23 is gradually formed toward an outer side of the concave portion 23 as the side surface 24 approaches an uncut surface of the base material 21. That is, the side surface 24 is inclined in a direction including an X direction component and a Y direction component. Also, a bottom surface 25 of the concave portion 23 is widened in the X direction in which the uncut surface of the base material 21 is widened. The surface to which the 690-type nickel-based alloy serving as the third welding material is built-up welded is the side surface 24 and the bottom surface 25 of the concave portion 23. The 690-type nickel-based alloy built-up welded to the side surface 24 and the bottom surface 25 of the concave portion 23 forms the joint cladding 26 described above. Consequently, in the modified example, a channel head 20b includes a cladding 22b and a base material 21b in which the concave portion 23 is formed and the joint cladding 26.

As described above, the breakdown in the boundary between the base material 21b and the joint cladding 26 in the welding structure may occur when the stress in the direction vertical to the boundary surface is greater than or equal to the fracture stress. Thus, in the stress analysis related to the steam generator of this modified example, the stress, in the direction vertical to the bottom surface 25, of the bottom surface 25 of the concave portion 23 and the stress, in the direction vertical to the side surface 24, of the side surface 24 of the concave portion 23 are obtained.

Figure 9:
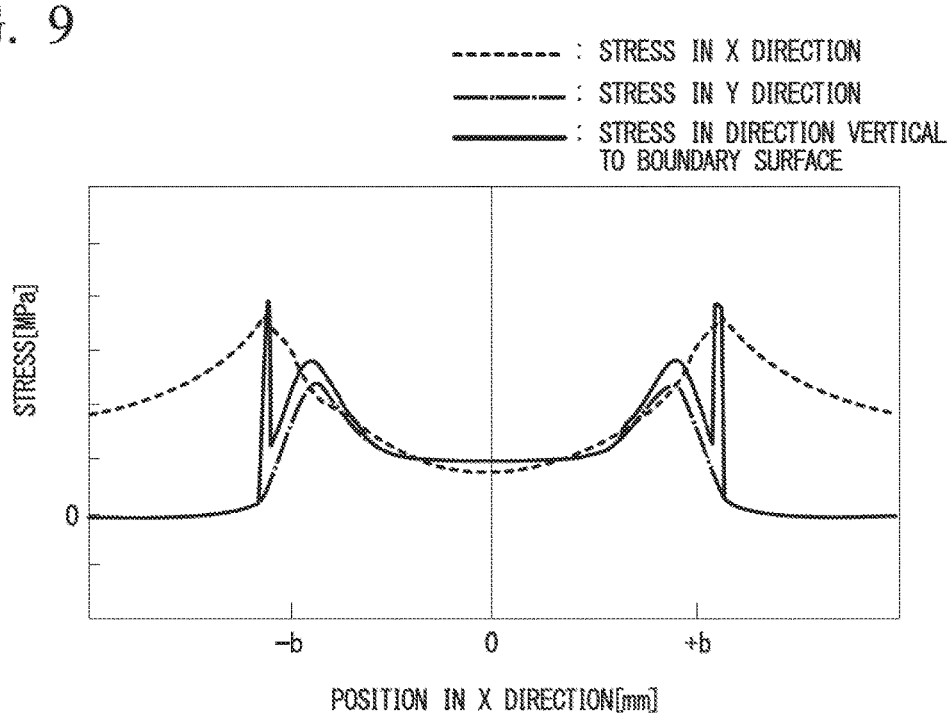
FIG. 9 is a graph illustrating the stress occurring at respective positions in the welding structure illustrated in FIG. 8.

Even in this stress analysis, as illustrated in FIG. 9, all maximum values of the stress in the X direction, the stress in the Y direction, the stress in the direction vertical to the boundary surface between the base material 21b and the joint cladding 26 occur in the vicinity of stress concentration positions. Also, in FIG. 9, a broken line represents the stress in the X direction, a one-dot chain line represents the stress in the Y direction, and a solid line represents the stress in the direction vertical to the boundary surface between the base material 21b and the joint cladding 26. As illustrated in FIG. 8, this stress concentration position is a contact position b between the surface of the joint cladding (third welding member) 26 formed of the third welding material (690-type nickel-based alloy) and the surface of the second welding member 27 formed of the second welding material (690-type nickel-based alloy).

If the fracture stress obtained in the characteristic stress acquisition step S4 in relation to the welding structure formed of the base material 21b formed of the low-alloy steel and the joint cladding (third welding member) 26 formed of the 690-type nickel-based alloy (third welding material) is 310 MPa and the maximum stress in the direction vertical to the boundary surface obtained in the stress analysis is 350 MPa and is greater than or equal to the fracture stress, the maximum stress in the direction vertical to the boundary surface is redesigned to be less than the fracture stress.

In this case, the following three methods are specifically considered.

First method: as in the above embodiment, a distance in the Y direction from the above-described stress concentration position b to the boundary between the base material 21b and the joint cladding 26 increases by increasing the thickness (a dimension in the Y direction) of the joint cladding 26 formed of the third welding material. In other words, the depth of the concave portion 23 is deepened.

Figure 10:
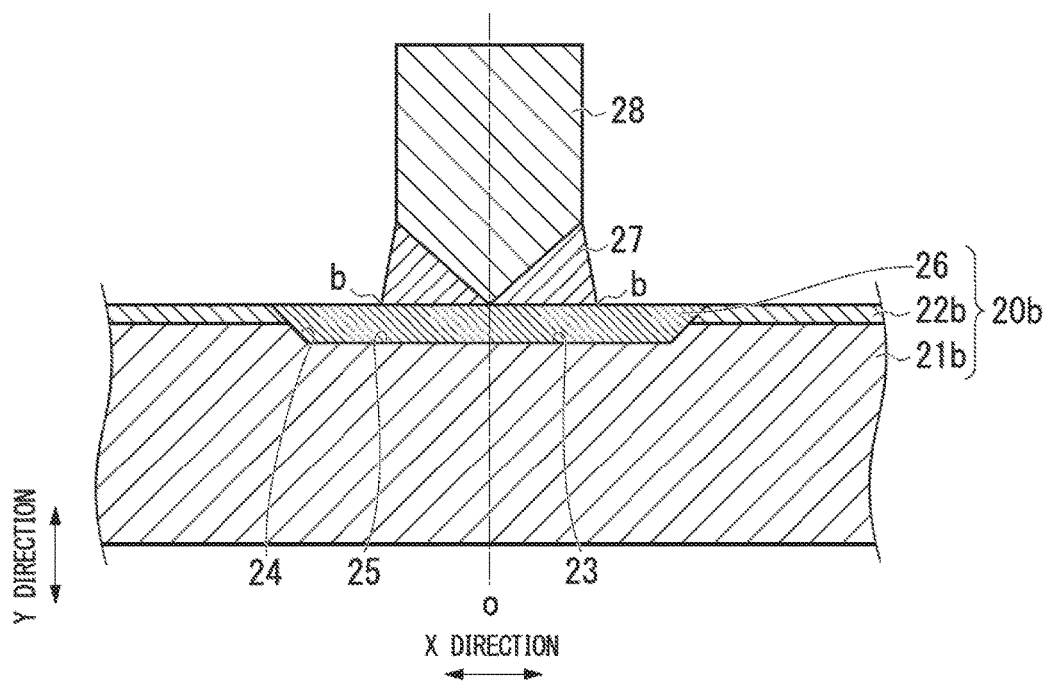
FIG. 10 is a cross-sectional view after a change in a design of the welding structure in a modified example of the embodiment according to the present invention.

Second method: as illustrated in FIG. 10, a distance in the Y direction from the above-described stress concentration position b to the boundary between the base material 21b and the joint cladding 26 increases by separating a region in the X direction of the side surface 24 of the concave portion 23 from the above-described stress concentration position b in the X direction. In other words, a width of the X direction of the concave portion 23 is widened.

Figure 11:
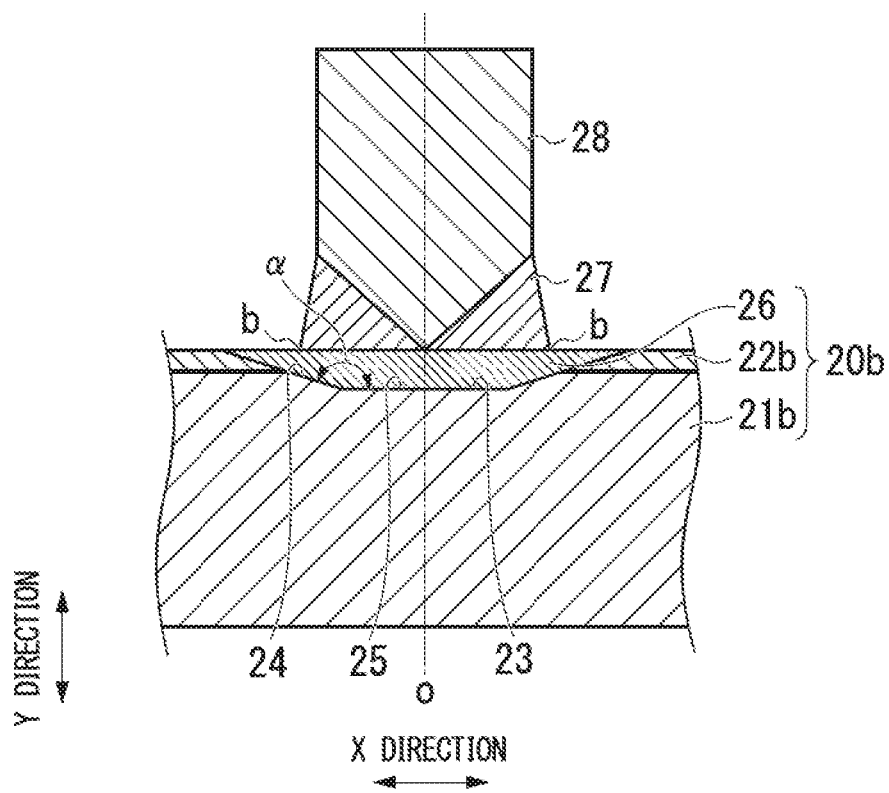
FIG. 11 is a cross-sectional view after a change in another design of the welding structure in a modified example of the embodiment according to the present invention.

Third method: as illustrated in FIG. 11, a stress component acting in the direction vertical to the boundary surface in a combined stress determined by the stress in the X direction and the stress in the Y direction acting in the boundary between the base material 21b and the joint cladding 26 is reduced by increasing an angle α of the side surface 24 relative to the bottom surface 25 of the concave portion 23.

Although each of the above three methods may be independently executed, two methods of the three methods may be combined and executed or all the three methods may be combined and executed.

All the above embodiments and the above-described modified examples are examples in which the present invention is applied to the welding structure of the channel heads 20 and 20b of the steam generator 3. However, any position may be possible in any welding structure, and, for example, the present invention may be applied to the welding structure of the nozzles 29i and 29o and the safe ends 31i and 31o of the steam generator 3.

Also, all the above embodiments and the above-described modified examples are examples in which the present invention is applied to the steam generator 3 serving as the welded structure. However, the present invention may be applied to the pressurizer 2 which is one of pressure vessels among devices constituting a nuclear power plant. Also, the welded structure is not limited to the devices in the nuclear power plant, but may be a device of another plant or the like.

As long as the first member is low-alloy steel or low-carbon steel and the welding material welded to the first member is a welding structure which is an austenitic alloy, the present invention may be applied to any welding structure. For example, the welding material may be austenitic stainless such as SUS 304 or SUS 316, a 600-type nickel-based alloy, or a 625-type nickel-based alloy.

In the above embodiment, a tensile test in which a rod-shaped test piece 50 is formed in the test piece creation step S2 and a load is applied in a direction in which two members are separated in the characteristic stress acquisition step S4 is performed. However, a bending test in which a plate-shaped test piece is formed in the test piece creation step S2 and a bending load is applied to the test piece in the characteristic stress acquisition step S4 may be performed.

In the hydrogen supply step S3 of the above embodiment, a test piece is immersed in an aqueous solution including hydrogen ions and hydrogen is supplied to the test piece. However, a hydrogen gas may be supplied to the test piece by arranging the test piece within a pressure vessel and supplying a high-pressure hydrogen gas into the pressure vessel. It is preferable to execute a pre-charging step and a charging step during the test as in the above embodiment even when the high-pressure hydrogen gas is supplied to the test piece.

INDUSTRIAL APPLICABILITY

According to an aspect of the present invention, it is possible to obtain a characteristic stress of a welding structure in which a welding material formed of an austenitic alloy is welded to a member formed of low-alloy steel or low-carbon steel. Consequently, it is possible to suppress damage to the welding structure by hydrogen embrittlement by designing and manufacturing a welded structure on the basis of the characteristic stress.

REFERENCE SIGNS LIST

1 Nuclear reactor
3 Steam generator
20, 20b Channel head
21, 21b Base material (first member)
22, 22b Cladding (first welding member)
23 Concave portion
24 Side surface (of concave portion)
25 Bottom surface (of concave portion)
26 Joint cladding (third welding member)
27 Second welding member
28 Partition plate (second member)
50 Test piece
53 Test piece base material
61 Test liquid (aqueous solution)
62 Counter electrode
63 Potentiostat

The invention claimed is:

1. A method of designing a welded structure, the method comprising:
    a test piece preparation step of preparing a test piece including a welding structure in which a welding material formed of an austenitic alloy is welded to a member formed of low-alloy steel or low-carbon steel;
    a hydrogen supply step of supplying hydrogen to the test piece;
    a characteristic stress acquisition step of applying a load to the test piece to which hydrogen was supplied and acquiring the characteristic stress showing material mechanical properties of the test piece; and
    a design step of designing the welded structure so that maximum stress occurring in the welding structure is less than the characteristic stress determined in the method of determining the characteristic stress of the welding structure in welded structures including the welding structure,
    wherein the welded structure includes a first member formed of the low-alloy steel or the low-carbon steel, a first welding member formed of a first welding material serving as the welding material built-up welded to the surface of the first member, and a second member welded to the surface of the first welding member via a second welding material,
    wherein the first member has a concave portion formed in the member formed of the low-alloy steel or the low-carbon steel by cutting a surface of the member and a side surface of the concave portion is inclined gradually toward an outer side of the concave portion as the side surface of the concave portion approaches an uncut surface,
    wherein the surface of the first member for built-up welding the first welding material is a bottom surface and a side surface of the concave portion, and
    wherein, in the design step, a region in which there is a side surface of the concave portion in a first direction in which a surface around the concave portion is widened is separated from a position in the first direction in which a surface of a second welding member formed of the second welding material is in contact with a surface of the first welding member.

2. The method of designing the welded structure according to claim 1, wherein the hydrogen supply step is executed while the characteristic stress acquisition step is executed.

3. The method of designing the welded structure according to claim 1, wherein the hydrogen supply step is executed before the characteristic stress acquisition step is executed.

4. The method of designing the welded structure according to claim 1, wherein the hydrogen supply step is continuously executed while the characteristic stress acquisition step is executed, from a time before the execution of the characteristic stress acquisition step.

5. The method of designing the welded structure according to claim 1, wherein, in the hydrogen supply step, the hydrogen is supplied to the test piece by arranging the test piece in an aqueous solution including hydrogen ions and setting the test piece as a negative electrode.

6. The method of designing welded structure according to claim 1,
wherein, in the hydrogen supply step, the hydrogen is supplied to the test piece by arranging the test piece in an aqueous solution including hydrogen ions and setting the test piece as a negative electrode, and
wherein, according to the execution of the hydrogen supply step, a hydrogen supply condition including an execution time of the hydrogen supply step to be executed before the characteristic stress acquisition step is determined so that a hydrogen concentration of a part formed of the low-alloy steel or the low-carbon steel in the test piece is greater than or equal to a maximum hydrogen concentration in a part of the first member, the part being on a boundary side with the first welding member.

7. The method of designing the welded structure according to claim 1, wherein, after a test piece base material including the welding structure in which the welding material is welded to the member formed of low-alloy steel or low-carbon steel is prepared in the test piece preparation step, a part including a boundary between the low-alloy steel or the low-carbon steel and the welding material is acquired as the test piece from the test piece base material.

8. The method of designing the welded structure according to claim 1, wherein the characteristic stress acquired in the characteristic stress acquisition step is fracture stress.

9. The method of designing the welded structure according to claim 1, wherein the welded structure is a pressure vessel.

10. The method of designing the welded structure according to claim 9, wherein the pressure vessel is a vessel in which coolant in a nuclear power plant is accumulated.

11. A method of manufacturing a welded structure, the method comprising:
the method of designing the welded structure according to claim 1; and
a manufacturing step of manufacturing the welded structure according to a result of executing the design method.

12. A method of designing a welded structure, the method comprising:
a test piece preparation step of preparing a test piece including a welding structure in which a welding material formed of an austenitic alloy is welded to a member formed of low-alloy steel or low-carbon steel;
a hydrogen supply step of supplying hydrogen to the test piece;
a characteristic stress acquisition step of applying a load to the test piece to which hydrogen was supplied and acquiring the characteristic stress showing material mechanical properties of the test piece; and
a design step of designing the welded structure so that maximum stress occurring in the welding structure is less than the characteristic stress determined in the method of determining the characteristic stress of the welding structure in welded structures including the welding structure,
wherein the welded structure includes a first member formed of the low-alloy steel or the low-carbon steel, a first welding member formed of a first welding material serving as the welding material built-up welded to the surface of the first member, and a second member welded to the surface of the first welding member via a second welding material,
wherein the first member has a concave portion formed in the member by cutting a surface of the member formed of the low-alloy steel or the low-carbon steel, a side surface of the concave portion is inclined gradually toward an outer side of the concave portion as the side surface of the concave portion approaches an uncut surface, and a bottom surface of the concave portion is widened in the first direction in which a surface around the concave portion is widened,
wherein the surface of the first member for built-up welding the first welding material is the bottom surface and the side surface of the concave portion, and
wherein an angle formed by the side surface inclined to the bottom surface of the concave portion is determined so that a maximum stress occurring in the welding structure of the welded structure is less than the characteristic stress in the design step.

13. The method of designing the welded structure according to claim 12, wherein the hydrogen supply step is executed while the characteristic stress acquisition step is executed.

14. The method of designing the welded structure according to claim 12, wherein the hydrogen supply step is executed before the characteristic stress acquisition step is executed.

15. The method of designing the welded structure according to claim 12, wherein the hydrogen supply step is continuously executed while the characteristic stress acquisition step is executed, from a time before the execution of the characteristic stress acquisition step.

16. The method of designing the welded structure according to claim 12, wherein, in the hydrogen supply step, the hydrogen is supplied to the test piece by arranging the test piece in an aqueous solution including hydrogen ions and setting the test piece as a negative electrode.

17. The method of designing the welded structure according to claim 12,
wherein, in the hydrogen supply step, the hydrogen is supplied to the test piece by arranging the test piece in an aqueous solution including hydrogen ions and setting the test piece as a negative electrode, and
wherein, according to the execution of the hydrogen supply step, a hydrogen supply condition including an execution time of the hydrogen supply step to be executed before the characteristic stress acquisition step is determined so that a hydrogen concentration of a part formed of the low-alloy steel or the low-carbon steel in the test piece is greater than or equal to a maximum hydrogen concentration in a part of the first member, the part being on a boundary side with the first welding member.

18. The method of designing the welded structure according to claim 12, wherein, after a test piece base material including the welding structure in which the welding material is welded to the member formed of low-alloy steel or low-carbon steel is prepared in the test piece preparation step, a part including a boundary between the low-alloy steel or the low-carbon steel and the welding material is acquired as the test piece from the test piece base material.

19. The method of designing the welded structure according to claim 12, wherein the characteristic stress acquired in the characteristic stress acquisition step is fracture stress.

20. The method of designing the welded structure according to claim 12, wherein the welded structure is a pressure vessel.

21. The method of designing the welded structure according to claim 20, wherein the pressure vessel is a vessel in which coolant in a nuclear power plant is accumulated.

22. A method of manufacturing a welded structure, the method comprising:
   the method of designing the welded structure according to claim 12; and
   a manufacturing step of manufacturing the welded structure according to a result of executing the design method.

* * * * *